(12) United States Patent
Chung et al.

(10) Patent No.: US 9,079,837 B2
(45) Date of Patent: Jul. 14, 2015

(54) WATER-SOLUBLE FLUORESCENT FULLERENE DERIVATIVE, AND PREPARATION METHOD THEREOF

(75) Inventors: Bong Hyun Chung, Daejeon (KR); Jin Young Jeong, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 315 days.

(21) Appl. No.: 13/643,292

(22) PCT Filed: Apr. 25, 2011

(86) PCT No.: PCT/KR2011/002991
§ 371 (c)(1),
(2), (4) Date: Nov. 15, 2012

(87) PCT Pub. No.: WO2011/136521
PCT Pub. Date: Nov. 3, 2011

(65) Prior Publication Data
US 2013/0102812 A1 Apr. 25, 2013

(30) Foreign Application Priority Data
Apr. 28, 2010 (KR) .......................... 10-2010-0039364

(51) Int. Cl.
*C07C 41/06* (2006.01)
*C09K 11/06* (2006.01)
*B82Y 30/00* (2011.01)

(52) U.S. Cl.
CPC ................. *C07C 41/06* (2013.01); *C09K 11/06* (2013.01); *B82Y 30/00* (2013.01); *C07C 2104/00* (2013.01); *C09K 2211/1011* (2013.01); *Y10S 977/74* (2013.01); *Y10S 977/847* (2013.01)

(58) Field of Classification Search
None
See application file for complete search history.

(56) References Cited

U.S. PATENT DOCUMENTS

| 6,506,928 | B1 | 1/2003 | Hirsch |
| 2004/0068207 | A1 | 4/2004 | Tabata |
| 2008/0004345 | A1 | 1/2008 | Tabata et al. |

FOREIGN PATENT DOCUMENTS

WO WO2006065243 A1 * 6/2006 .............. C07C 69/74

OTHER PUBLICATIONS

Yifeng et al. (Journal of Materials Chemistry, published online Nov. 8, 2010, printed 2011, Issue 21, pp. 819-823).*
J. Liu et al. (Journal of Controlled Release, vol. 117, 2007, pp. 104-110).*
Hu et al. (Chinese Chemical Letters, vol. 18, 2007, pp. 51-54).*
(Continued)

*Primary Examiner* — Rosalynd Keys
(74) *Attorney, Agent, or Firm* — Hultquist, PLLC; Steven J. Hultquist (57) ABSTRACT

A simple and easy method is described for preparing a water-soluble fluorescent fullerene derivative with strong fluorescence and hydrophilicity, by mixing fullerene and a ligand containing a terminal hydroxyl group in a first solvent and reacting the mixture in the presence of a catalyst. Such preparation method enables the intensity and wavelength of fluorescence to be easily controlled depending on the amount of fullerene and the type of catalyst that are utilized. The prepared fluorescent fullerene derivative contains a biocompatible ligand, and thus is useful as a biological fluorescent dye. As a result of its fluorescence and excellent solubility in solvent, the fluorescent fullerene derivative is useful in biological, medical, nanotechnology, and other fields.

8 Claims, 8 Drawing Sheets

(56) References Cited

OTHER PUBLICATIONS

Manolova et al. (J. Chem. Soc. Commun., 1993, pp. 1725-1727).*

Anderson, J., et al., "Photophysical Characterization and Singlet Oxygen Yield of a Dihydrofullerene", "J. Am. Chem. Soc.", Oct. 1994, pp. 9763-9764, vol. 116.

Chiang, L, et al., "Efficient One-Flask Synthesis of Water-Soluble [60]Fullerenols", "Tetrahedron", Apr. 1, 1996, pp. 4963-4972, vol. 52, No. 14.

Cho, S., et al., "Long-Term Exposure to CdTe Quantum Dots Causes Functional Impairments in Live Cells", "Langmuir", Jan. 12, 2007, pp. 1974-1980, vol. 23.

Hawker, C., et al., "The Synthesis and Characterization of a Self-Assembling Amphiphilic Fullerene", "J. Org. Chem.", Jun. 1994, pp. 3503-3505, vol. 59.

Kojima, C., et al., "Aqueous Solubilization of Fullerenes Using Poly(amidoamine) Dendrimers Bearing Cyclodextrin and Poly(ethylene Glycol)", "Bioconjugate Chem.", Oct. 10, 2008, pp. 2280-2284, vol. 19.

Li, J., et al., "C60 Fullerol Formation catalysed by Quaternary Ammonium Hydroxides", "Journal of the Chemical Society, Chemical Communications", 1993, pp. 1784-1785.

Sun, Y., et al., "Fluorescence Spectra and Quantum Yields of Buckminsterfullerene (C60) in Room-Temperature Solutions. No Excitation Wavelength Dependence", "J. Am. Chem. Soc.", Jul. 1993, pp. 6378-6381, vol. 115.

Tang, Z., et al., "Synthesis and Characterization of Monolayers and Langmuir-Blodgett Films of an Amphiphilic Oligo(ethylene glycol)-C60-hexadecaaniline Conjugate", "Langmuir", Apr. 26, 2006, pp. 5366-5373, vol. 22.

Wakai, H., et al., "Grafting of poly(ethylene oxide) onto C60 fullerene using macroazo initiators", "Polymer", Feb. 12, 2007, pp. 1972-1980, vol. 48.

Wang, Y., et al., "Hollow porous carbon nanospheres with large surface area and stability, assembled from oxidized fullerenes", "Journal of Materials Chemistry", Jan. 11, 2005, pp. 1049-1054, vol. 15.

Note: For the non-patent literature citations that no month of publication is indicated, the year of publication is more than 1 year prior to the effective filing date of the present application.

* cited by examiner

WATER-SOLUBLE FLUORESCENT FULLERENE DERIVATIVE, AND PREPARATION METHOD THEREOF

CROSS-REFERENCE TO RELATED APPLICATIONS

This application is a U.S. national phase under the provisions of 35 U.S.C. §371 of International Patent Application No. PCT/KR11/02991 filed Apr. 25, 2011, which in turn claims priority of Korean Patent Application No. 10-2010-0039364 filed Apr. 28, 2010. The disclosures of such international patent application and Korean priority patent application are hereby incorporated herein by reference in their respective entireties, for all purposes.

TECHNICAL FIELD

The present invention relates to a water-soluble fluorescent fullerene derivative and a preparation method thereof, and more particularly to a method of preparing a fullerene derivative having excellent fluorescence in a simple manner by mixing fullerene and a ligand containing a terminal hydroxyl group in a first solvent and reacting the mixture in the presence of a catalyst, and to a water-soluble fluorescent fullerene derivative prepared by the method.

BACKGROUND ART

Generally, fullerenes are spherical molecules composed of 5- and 6-membered rings, which are attached to each other and have carbon-carbon double bonds. Due to their unique structures, fullerenes are highly applicable in industrial fields, including medical fields related to diseases such as Alzheimer's disease, or free radicals, and nanotechnology fields.

In particular, buckminster fullerene ($C_{60}$) is a stable carbon molecule consisting of 60 carbon atoms and having a spherical structure and possesses an icosahedral symmetry, and thus all the carbon environments are identical. This was confirmed by a single peak in C-NMR. In addition to the $C_{60}$ fullerene, $C_{70}$ and $C_{80}$ fullerenes are also synthesized, but the amount of synthesis thereof are not large, and thus the $C_{60}$ fullerene has been mainly synthesized and studied.

Fullerene molecules are symmetrical non-polar molecules having a substantially spherical structure and do not dissolve in polar solvents such as water or alcohols and easily dissolve in non-polar solvents such as benzene or toluene. Further, fullerenes are very sensitive to light and can be easily converted to radicals or light sensitizers, because they become an excited state when they exposed to light. The electrochemical properties of fullerenes are very useful, and the fullerene molecules can undergo 6 reversible oxidation-reduction reactions and are very hard because of their unique structures. In recent years, it was reported that fullerene molecules can be converted to superconductors when they are mixed with alkali metals, and thus the industrial applicability thereof is high.

As described above, fullerenes are very sensitive to light, and the light absorbance in the UV region (213, 257 and 329 nm) is relatively high. However, the fluorescence of fullerenes is known to be very low and can be given by the fluorescence quantum yield. The term "fluorescence quantum yield" refers to the number of emitted photons relative to the number of absorbed photons, and the quantum yield of fullerenes is shown to be about $1\times10^{-4}$ at room temperature. Due to this low fluorescence efficiency, the fluorescence of fullerenes has not been applied.

In addition, fullerenes have unique optical and electrical properties, but there are several difficulties in applying fullerenes. The difficulties include low solubility in organic solvents, self-aggregation phenomena, etc. In particular, fullerenes are very sensitive to surrounding environments, and thus the physical and chemical properties thereof easily change. To control such characteristics, various methods have been developed.

To apply fullerenes in the biological field, the medical field, the nanotechnology field and the like, it is required that fullerenes easily dissolve in water (water-soluble properties). Thus, it is particularly important to prepare water-soluble fullerenes.

Typical methods for preparing water-soluble fullerenes include a method of preparing fullerol by introducing a hydroxyl group (OH) to the surface of fullerene through a chemical reaction [*Tetrahedron*, (1996) 52, 4963-4972; *Chem. Comm.*, (1993) 1784; *J. Mater. Chem.*, (2005) 15, 1049], a method of introducing oligoethylene glycol or polyethylene, modified with a ligand capable of binding to fullerenes [*Langmuir*, (2006), 22, 5366-537; *Polymer*, (2007) 48, 1972-1980; *Bioconjugate Chem.*, (2008) 19, 2280-2284], etc. However, such methods have problems in that these preparation methods are complicated, because many synthesis steps are required for binding to fullerenes, and the utility of the prepared fullerenes is significantly low, because the solubility thereof in water is not high.

Thus, many researchers are recognizing that developing water-soluble fluorescent fullerenes having high solubility in water and unique optical properties (such strong fluorescence) by a simple reaction is important in increasing the utility of fullerenes in the biological field, the medical field and the nanotechnology field.

Accordingly, the present inventors have made extensive efforts to solve the above-described problems occurring in the prior art and, as a result, have found that a water-soluble fullerene derivative having strong fluorescence can be prepared in a simple and easy manner by mixing fullerene with a ligand having a terminal hydroxyl group in a first solvent and then reacting the mixture in the presence of a catalyst, thereby completing the present invention.

DISCLOSURE OF INVENTION

Technical Problem

It is a main object of the present invention to provide a method for preparing a fullerene derivative having excellent biocompatibility, hydrophilicity and strong fluorescence in a simple manner, and a water-soluble fluorescent fullerene derivative prepared by the above method.

Technical Solution

To achieve the above object, the present invention provides a method for preparing a water-soluble fluorescent fullerene derivative, the method comprising the steps of: (a) dispersing fullerene in a first solvent to obtain a dispersion; (b) mixing the dispersion with a catalyst and a ligand containing a terminal hydroxyl group to obtain a mixture; and (c) purifying the mixture, thereby preparing a fluorescent fullerene derivative.

The present invention also provides a water-soluble fluorescent fullerene derivative prepared by the above method and comprising a ligand containing a terminal hydroxyl group.

The present invention also provides a water-soluble fluorescent fullerene derivative comprising fullerene bound to a ligand by —C—O—.

Other features and embodiments of the present invention will be more apparent from the following detailed descriptions and the appended claims.

BRIEF DESCRIPTION OF THE DRAWINGS

FIG. 5 is a set of photographs showing water-soluble fluorescent fullerene derivatives prepared from various concentrations of a $C_{60}$ fullerene. In FIG. 5, (a): a photograph in white light; and (b): a photograph taken in UV light.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The definition of main terms used in the detailed description of the invention is as follows.

As used herein, the term "fluorescent fullerene derivative" refers to a fullerene derivative that emits light by excitation of light.

In one aspect, the present invention is directed to a method for preparing a water-soluble fluorescent fullerene derivative, the method comprising the steps of: (a) dispersing fullerene in a first solvent to obtain a dispersion; (b) mixing the dispersion with a catalyst and a ligand containing a terminal hydroxyl group to obtain a mixture; and (c) purifying the mixture, thereby preparing a fluorescent fullerene derivative.

Figure 1:
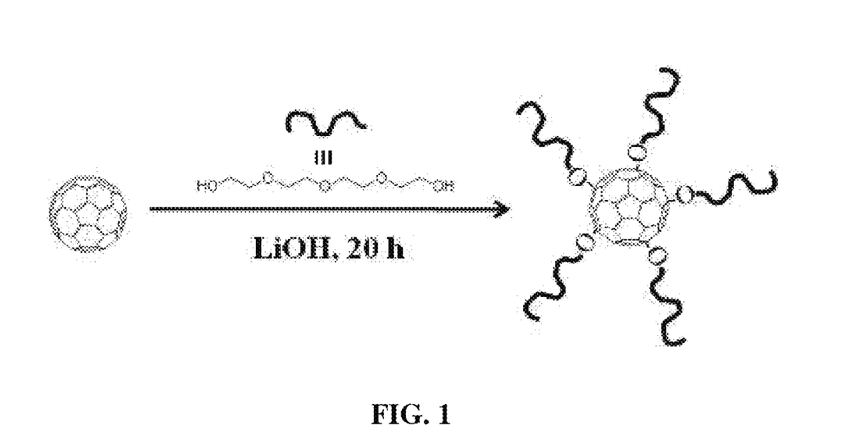
FIG. 1 is a schematic diagram showing a method for preparing a water-soluble fluorescent fullerene derivative according to the present invention.

Specifically, as shown in FIG. 1, a water-soluble fluorescent fullerene derivative having strong fluorescence according to the present invention can be prepared in a simple manner by a method comprising mixing fullerene with a ligand containing a terminal hydroxyl group in a first solvent and then reacting the mixture in the presence of a catalyst as a strong base. The intensity and wavelength of fluorescence can be easily controlled depending on the amount of fullerene and the kind of catalyst.

Further, the water-soluble fluorescent fullerene derivative prepared by the above preparation method contains a biocompatible ligand, and thus can be advantageously used as a biological fluorescent dye. In addition, it has fluorescence and excellent solubility in a solvent, and thus can be advantageously used in the biological field, the medical field, the nanotechnology field, and the like.

In the present invention, in addition to a $C_{60}$ fullerene, fullerenes belonging to the fullerene family, such as $C_{70}$, $C_{80}$ and $C_{90}$ fullerenes, may be used. As used herein, the term "fullerene family" correctively refers to molecules which consist entirely of carbon atoms and are spherically symmetrical. Some fullerenes having a large number of carbon atoms cannot be perfectly symmetrical, and a dispersion of fullerene in the first solvent may also be used in the present invention.

The first solvent functions to disperse fullerene. Any solvent may be used as the first solvent, as long as it can disperse fullerene. Preferably, the first solvent is selected from the group consisting of aromatic organic solvents, such as toluene or benzene, cyclohexane, heptane, iso-ocatane, and mixtures thereof.

In the preparation method of the present invention, fullerene is dispersed in the first solvent to a concentration of 0.0001 mg/ml to 10 mg/ml. If the concentration of fullerene is less than 0.0001 mg/ml, the resulting fullerene derivative will not be useful because the intensity of fluorescence thereof will be low, and if the concentration of fullerene is more than 10 mg/ml, the reactivity of fullerene by the catalyst will be reduced.

In addition, with respect to the control of fluorescence intensity and wavelength by the amount of fullerene added, as the amount of fullerene added increases, the wavelength of fluorescence emitted from the resulting fluorescent fullerene becomes longer and the intensity of fluorescence also decreases, and as the amount of fullerene added to the first solvent decreases, the wavelength of fluorescence emitted from the resulting fluorescent fullerene becomes shorter and the intensity of fluorescence also increases. Thus, the intensity and wavelength of fluorescence can be controlled by increasing or decreasing the amount of fullerene added to the first solvent.

In the present invention, the ligand containing a terminal hydroxyl group is preferably a compound containing an ethyleneglycol group. A compound containing 2 to several hundred ethyleneglycol groups may be used as the ligand, but is not limited. As the ligand, any compound can be used as long as it has high solubility in the first solvent having fullerene dispersed therein, does not agglomerate fullerene and contains one or more hydroxyl groups at one or both ends thereof.

The ligand containing a terminal hydroxyl group according to the present invention is preferably selected from the group consisting of diethylene glycol, triethylene glycol, tetraethylene glycol, hexaethylene glycol, poly-ethylene glycol having molecular weights of 200, 300, 400 and 600, ethanolamine, diethanolamine, 2-(Benzyloxy)ethanol, 2-(butylamino)ethanol, 2-(cyclohexyloxy)ethanol, 2-(dibutylamino)ethanol, 2-(diisopropylamino)ethanol, 2-(diethylamino)ethanol, 2-[2-(dimethylamino)ethoxy]ethanol, di(ethylene glycol)benzylether, di(ethylene glycol)ethylether], di(ethylene glycol)hexylether], diethylene glycol butylether, diethylene glycol methylether, diethylene glycol monobutylether, diethylene glycol monoethylether), diethylene glycol monomethylether), 2-(2-ethylhexyloxy)ethanol], 2-(3,4-dimethoxyphenyl)ethanol, and mixtures thereof.

In the present invention, the catalyst functions to induce the chemical binding between the ligand containing a terminal hydroxyl group and fullerene dispersed in the first solvent. Any catalyst may be used without limitation, as long as it is a strong base. The catalyst is preferably selected from the group consisting of lithium hydroxide (LiOH), sodium hydroxide (NaOH), potassium hydroxide (KOH), calcium hydroxide ($Ca(OH)_2$), magnesium hydroxide ($Mg(OH)_2$), barium hydroxide, cadmium hydroxide, cesium hydroxide, cobalt hydroxide, copper hydroxide, nickel hydroxide, rubidium hydroxide, ammonium hydroxide, tetramethylammonium hydroxide, tetraethylammonium hydroxide, tetrabutyl ammonium hydroxide, tetrahexylammonium hydroxide, benzyltrimethylammonium hydroxide, hexadecyltrimethylammonium hydroxide, diethyldimethylammonium hydroxide, and mixture thereof.

In the preparation method according to the present invention, with respect to the ratio of mixing of the dispersion containing fullerene dispersed in the first solvent, the ligand containing a terminal hydroxyl group, and the catalyst, the ligand containing the terminal hydroxyl group, and the catalyst are used in the amounts of 0.0001-100 parts by weight and 0.0001-100 parts by weight, respectively, based on 100 parts by weight of the dispersion containing fullerene dispersed in the first solvent.

If the ligand containing the terminal hydroxyl group is used in an amount of less than 0.0001 parts by weight based on 100 parts by weight of the dispersion containing fullerene dispersed in the first solvent, the content of the ligand bound to fullerene will be low, and thus it cannot solubility in the solvent, and if the ligand is used in an amount of more than 100 parts by weight, the amount of unreacted ligand will increase.

Meanwhile, if the catalyst is used in an amount of less than 0.0001 parts by weight based on 100 parts by weight of the dispersion containing fullerene dispersed in the first solvent, the catalyst cannot induce the reaction between fullerene and the ligand, and if the catalyst is used in an amount of more than 100 parts by weight, the will induce an unstable reaction.

In addition, in the present invention, the wavelength of fluorescence can be controlled depending on the kind of catalyst. The binding between the ligand and fullerene can be controlled depending on the reactivity induced by the catalyst. Specifically, as the reactivity increases, the wavelength of fluorescence becomes longer, and as the reactivity decreases, the wavelength of fluorescence becomes shorter.

The mixture prepared as described above is subjected to a purification process wherein the resulting water-soluble fluorescent fullerene derivative is precipitated using a second solvent selected from the group consisting of non-polar solvents, polar solvents, and mixtures thereof, and is separated from unreacted fullerene and the ligand containing the terminal hydroxyl group. The second solvent is selected from the group consisting of non-polar solvents such as toluene, benzene or hexane, polar solvents such as ethanol or methanol, and mixtures thereof. Preferably, an alcohol such as ethyl acetate or ethanol may be used as the second solvent.

The inventive method for preparing the water-soluble fluorescent fullerene derivative can prepare a fullerene derivative having strong fluorescence in a simple and easy manner and can easily control the intensity and wavelength of fluorescence depending on the amount of fullerene and the kind of catalyst.

In another aspect, the present invention is directed to a water-soluble fluorescent fullerene derivative comprising fullerene bound to a ligand by —C—O—.

In the process in which fullerene reacts with the ligand containing the terminal hydroxyl group in the presence of the catalyst, the carbon covalent bond of the fullerene is broken and binds to an oxygen atom, while the fullerene and the ligand are bound to each other by —C—O—. Thus, in the fluorescent fullerene derivative of the present invention, the UV absorbance wavelengths (220, 260 and 350 nm) of the fullerene itself disappear, and the fullerene derivative strongly absorbs light in the UV region (200-400 nm) while it emits strong fluorescence at 530 nm when it is irradiated with light at 350 nm. In addition, the fullerene derivative has excellent hydrophilicity and water dispersibility.

The solubility of the inventive fluorescent fullerene derivative in water is 100 mg/ml or less, preferably 0.1 mg/ml-20 mg/ml, at room temperature (25° C.). Thus, it can be seen that the water solubility of the fullerene derivative prepared in the present invention is much higher than that of a general $C_{60}$ fullerene having a solubility of $1.3 \times 10^{-11}$ mg/ml (Sivaraman, N. et al., *J. Org. Chem.*, 1992, 57, 6077-6079).

In addition, the fluorescent fullerene derivative according to the present invention has a fluorescence intensity of 200-1000 in a wavelength region of 500-550 nm and has a fluorescence quantum yield of $2 \times 10^{-3}$ to $5 \times 10^{-3}$, which is about 20-50 times higher than that of a general fullerene having a fluorescence quantum yield of $1 \times 10^{-4}$ (*J. Am. Chem. Soc.*, 115, 6378 (1993); *J. Am. Chem. Soc.*, 116, 9763 (1994)).

Therefore, the fluorescent fullerene derivative according to the present invention is useful in the biological field, the medical field, the nanotechnology field, etc.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Water-Soluble Fluorescent Fullerene Derivative of $C_{60}$ Fullerene A $C_{60}$ fullerene (MER Co.) was dispersed in toluene to a concentration of 2 mg/ml, and 10 ml of the dispersion was added to tetraethylene glycol (TEG) at a ratio of 1:1 such that the final concentration of the fullerene reached 0.12, 0.25, 0.5 and 1.0 mg/ml, followed by stirring. To the stirred mixture, 32 mg of lithium hydroxide (LiOH) was added to a concentration of 75 mM and stirred at room temperature for 20 hours. After the pink-colored fullerene in the stirred mixture has been confirmed to change to a brown color and the reaction has been completed, ethylene acetate was added to the mixture to induce the precipitation of the fluorescent fullerene derivative, and then the fluorescent fullerene derivative was separated by centrifugation. To the mixture from which the fluorescent fullerene derivative has been separated, a small amount of ethanol was added, and the process of adding an excess amount of ethylene acetate thereto to induce precipitation and separating the precipitate was further performed twice, thereby preparing dark-brown fluorescent derivatives of the $C_{60}$ fullerene.

Example 2

Preparation of Water-Soluble Fluorescent Fullerene Derivative of $C_{70}$ Fullerene A water-soluble fluorescent derivative of a $C_{70}$ fullerene was prepared in the same manner as Example 1, except that a $C_{70}$ fullerene (MER Co.) was added to tetraethylene glycol (TEG) such that the final concentration of the $C_{70}$ fullerene reached 1 mg/ml.

Example 3

Preparation of Water-Soluble Fluorescent Fullerene Derivative Using Diethyleneglycol as Ligand A water-soluble fluorescent fullerene derivative was prepared in the same manner as Example 1, except that $C_{60}$ fullerene was added to tetraethylene glycol such that the final concentration of the $C_{60}$ fullerene reached 1 mg/ml.

Test Example 1

Figure 2:
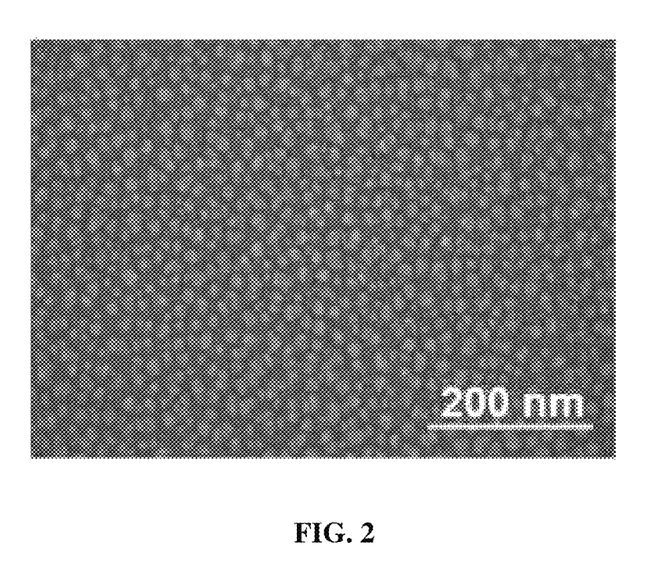
FIG. 2 is a SEM photograph of a water-soluble fluorescent fullerene derivative prepared from a $C_{60}$ fullerene according to the present invention.

Evaluation of Properties of Water-Soluble Fluorescent Fullerene Derivative of $C_{60}$ Fullerene Among the water-soluble fluorescent fullerene derivatives prepared in Example 1, the water-soluble fluorescent fullerene derivative prepared by adding the $C_{60}$ fullerene to tetraethylene glycol (TEG) so as to reach a final concentration of fullerene of 1 mg/ml was observed using a scanning electron microscope (SEM, FEI, Sirion, Netherland). As a result, as shown in FIG. 2, the fullerene derivative particles had an average diameter of about 10 nm.

Figure 3:
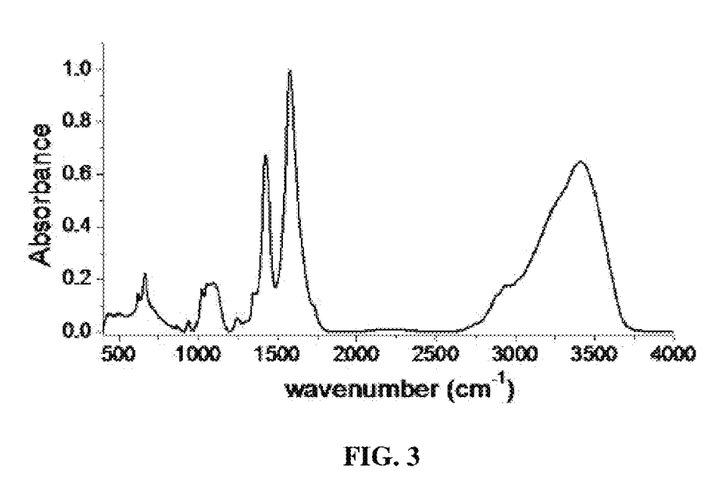
FIG. 3 is a graphic diagram showing the FT-IR spectrum of a water-soluble fluorescent fullerene derivative prepared from a $C_{60}$ fullerene according to the present invention.
Figure 4:
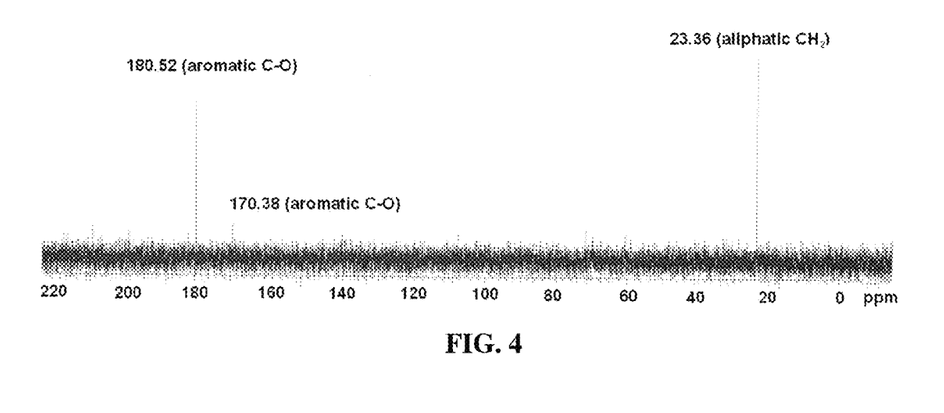
FIG. 4 is a graphic diagram showing the NMR spectrum of a water-soluble fluorescent fullerene derivative prepared from a $C_{60}$ fullerene according to the present invention.

Also, the water-soluble fluorescent fullerene derivative was measured by an IR spectrophotometer (Bruker Optics IF66). As a result, as shown in FIG. 3, absorption spectra appeared at 867 $cm^{-1}$ indicating C—O—C stretching vibration, 1090 $cm^{-1}$ indicating C—O stretching vibration, and 3426 $cm^{-1}$ indicating O—H stretching vibration, suggesting that oxygen was bound to aromatic carbon. Further, the fullerene derivative was analyzed by the NMR spectrum. As a result, as shown in FIG. 4, signals appeared at 23.36 indicating an alkyl structure of ethylene glycol, and 170.38 and 180.52 indicating a structure of oxygen bound to aromatic carbon, similar to the results of the IR spectrum.

Test Example 2

Figure 5:
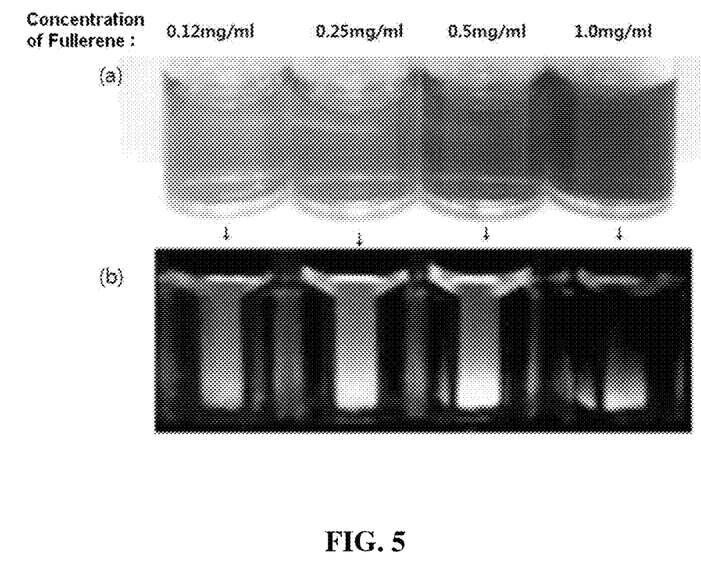

Measurement of Fluorescence of Water-Soluble Fluorescent Fullerene Derivative of $C_{60}$ Fullerene Each of the water-soluble fluorescent fullerene derivatives of the $C_{60}$ fullerene, prepared in Example 1, was dispersed in water, and then the fluorescence of the fluorescent fullerene derivative was measured by irradiation with UV light at a wavelength of 365 nm using a UV hand lamp (UV.F104L, UVITEC). As a result, as shown in FIG. 5, the fluorescent fullerene derivative of the $C_{60}$ fullerene, which a brown color (or a yellow color) in visible light, had a color ranging from blue to orange depending the amount of fullerene added, when it was irradiated with UV light. Thus, it could be seen that, as the concentration of the fullerene increased, the wavelength of emitted fluorescence became longer, and as the concentration of the fullerene decreased, the wavelength of emitted fluorescence became shorter.

Figure 6:
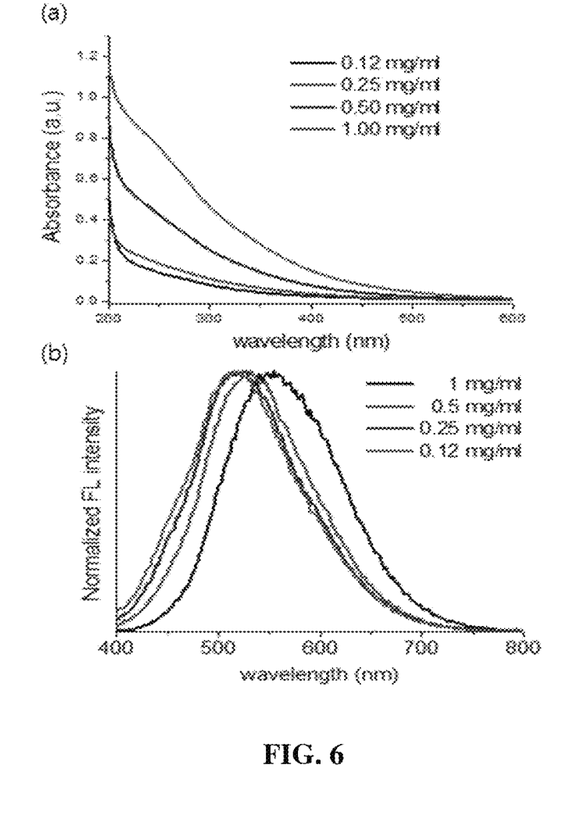
FIG. 6 is a set of photographs showing the absorption spectrum (a) and fluorescence spectrum (b) of a water-soluble fluorescent fullerene derivative prepared from a $C_{60}$ fullerene according to the present invention.

The absorption spectrum and fluorescence spectrum of each of the water-soluble fluorescent fullerene derivatives of the $C_{60}$ fullerene, prepared in Example 1, were measured. As a result, it was shown that the water-soluble fluorescent fullerene derivative according to the present invention strongly absorbed light in short-wavelength UV light (FIG. 6(*a*)), and when it was irradiated with UV light at 350 nm, it emitted fluorescence ranging from 500 nm to 550 nm depending on the concentration of the fullerene added (see FIG. 6(*b*)).

In addition, the fluorescence quantum yield of the water-soluble fluorescent fullerene derivative according to the present invention was measured and calculated in comparison with a quinine sulfate (QS, $55 \times 10^{-2}$) standard. First, for each concentration, five samples of each of the water-soluble fluorescent fullerene derivative (having an absorbance of 0.1 or less at 350 nm) of Example 1 and quinine sulfate were prepared, the samples at each concentration were excited at 350 nm, and then the fluorescence spectra at 400-700 nm were measured. In the same manner as above, the fluorescence spectrum of the standard quinine sulfate was measured and the fluorescence quantum yield thereof was calculated in comparison with that of the water-soluble fluorescent fullerene derivative.

As a result, it could be seen that the fluorescence quantum yield of the water-soluble fluorescent fullerene derivative according to the present invention was $2 \times 10^{-3}$, which is about 20 times higher than the fluorescence quantum yield ($1 \times 10^{-4}$) (*J. Am. Chem. Soc.*, 115, 6378 (1993); *J. Am. Chem. Soc.*, 116, 9763 (1994)) of the general fullerene.

Figure 7:
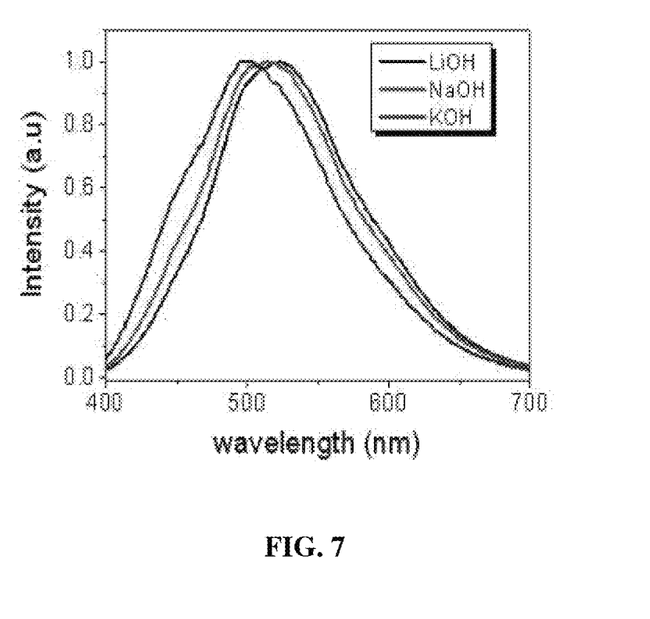
FIG. 7 is a graphic diagram showing the fluorescence spectra of water-soluble fluorescent fullerene derivatives prepared from a $C_{60}$ fullerene in the presence of various catalysts according to the present invention.

Meanwhile, water-soluble fluorescent fullerene derivatives were prepared in the same manner as Example 1, except that a $C_{60}$ fullerene was added to tetraethylene glycol (TEG) to reach a final $C_{60}$ fullerene concentration of 1 mg/ml and various catalysts (LiOH, NaOH and KOH) were added thereto. The fluorescence of each of the prepared water-soluble fluorescent fullerene derivatives was measured. As a result, as shown in FIG. 7, the wavelength of fluorescence emitted from the fullerene derivatives varied depending on the kind of catalyst.

Example 3

Figure 8:
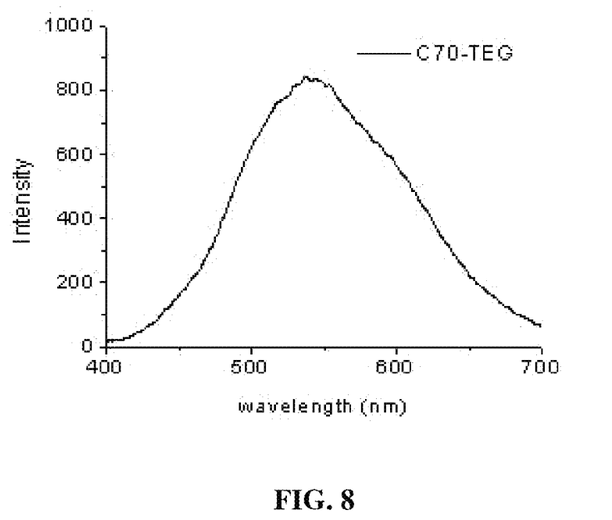
FIG. 8 is a graphic diagram showing the fluorescence spectrum of a water-soluble fluorescent fullerene derivative prepared from a $C_{70}$ fullerene according to the present invention.

Measurement of Fluorescence of Water-Soluble Fluorescent Fullerene Derivative of $C_{70}$ Fullerene The fluorescence spectrum of the water-soluble fluorescent fullerene derivative of the $C_{70}$ fullerene, prepared in Example 2, was measured. As a result, as shown in FIG. 8, the fullerene derivative prepared using the $C_{70}$ fullerene emitted light at a fluorescence intensity of 800 or higher at 540 nm when irradiated with UV light at 350 nm.

Test Example 4

Figure 9:
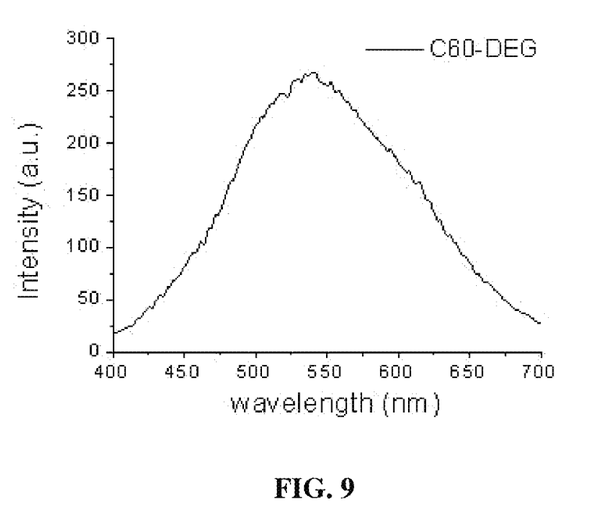
FIG. 9 is a graphic diagram showing the fluorescence spectrum of a water-soluble fluorescent fullerene derivative comprising a diethyleneglycol ligand according to the present invention.

Measurement of Fluorescence of Water-Soluble Fluorescent Fullerene Derivative Comprising Diethyleneglycol Ligand The fluorescence spectrum of the water-soluble fluorescent fullerene derivative of the $C_{60}$ fullerene, prepared in Example 3, was measured. As a result, as shown in FIG. 9, the fullerene derivative prepared using the $C_{60}$ fullerene emitted light at a fluorescence intensity of 250 or higher at 540 nm when irradiated with UV light at 350 nm.

Test Example 5

Figure 10:
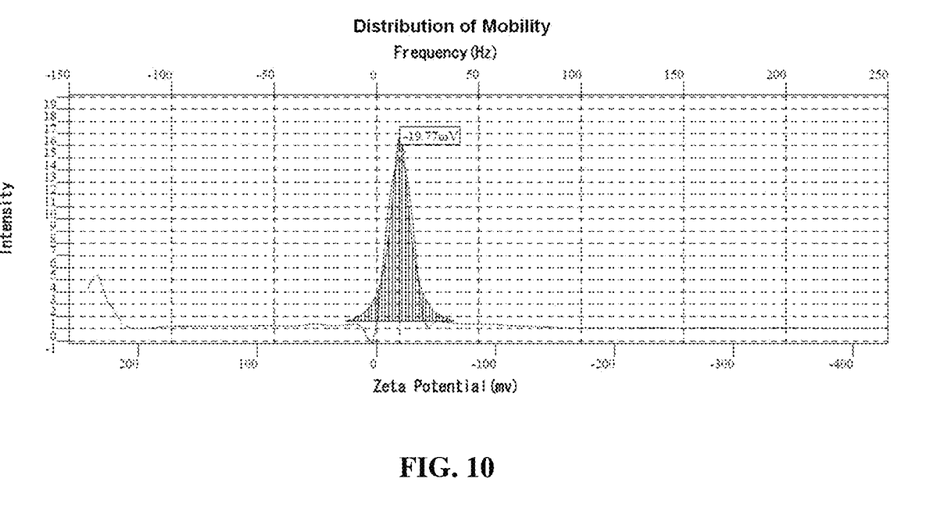
FIG. 10 is a graphic diagram showing the results of measuring the zeta-potential of a water-soluble fluorescent fullerene derivative according to the present invention.

Measurement of Solubility of Water-Soluble Fluorescent Fullerene Derivative in Water With respect to the dispersibility of the fluorescent fullerene derivative, the zeta-potential of the fluorescent fullerene derivative dispersed in water was measured by ELS-Z (Otska, Japan). The zeta-potential of the water-soluble fluorescent fullerene derivative of Example 1, prepared so as to reach a final $C_{60}$ fullerene (MER Co.) concentration of 1 mg/ml, was measured. As a result, as shown in FIG. 10, the zeta-potential was about −20 mV. This suggests that the water-soluble fluorescent fullerene derivative was negatively charged and easily dissolved in water. In addition, when the fullerene derivative dispersed in water at various concentrations was observed, it was present as a yellow solution without agglomeration at a high concentration of 20 mg/ml or less, suggesting that the dispersibility or solubility of the fullerene derivative in water is very high.

Test Example 6

Figure 11:
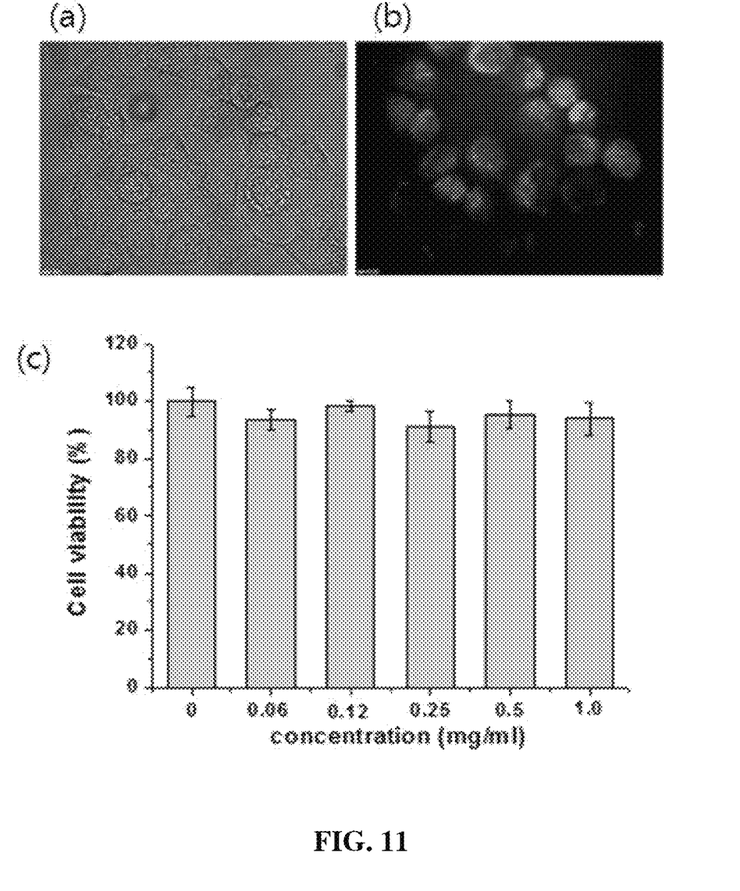
FIG. 11 shows cell imaging photographs (FIGS. 11a and 11b) and a cell viability graph (FIG. 11c), obtained using a water-soluble fluorescent fullerene derivative according to the present invention.

Cell Imaging and Cell Viability Measurement for Water-Soluble Fluorescent Fullerene Derivative In order to confirm the possibility of the inventive water-soluble fluorescent fullerene derivative as a bio-imaging material, the water-soluble fluorescent fullerene derivative prepared in Example 3 was penetrated into cervical cancer HeLa cells (KCLB 10002, Korean Cell Line Bank) and observed with a fluorescence microscope. FIG. 11(a) is a photograph of cells containing the water-soluble fluorescent fullerene derivative, and FIG. 11(b) is a fluorescence photograph obtained using a 525 nm filter by exciting light of 420 nm at the same position. As can be seen in FIG. 11(b), a green signal of the water-soluble fluorescent fullerene derivative could be observed at the same position as that in FIG. 11(a). In addition, in order to examine the cell viability of cells treated with the water-soluble fluorescent fullerene derivative, an MTT assay was performed. As a control group, cells free of the water-soluble fluorescent fullerene were used. Cells were treated with the water-soluble fluorescent fullerene derivative at varying concentrations of 0.06-1.0 mg/mL, and then the cell viability was compared between the treated cell group and the control group.

As a result, as shown in FIG. 11c, the cell viability of the cells treated with the treated cell group was similar to that of the control group over the entire concentration range. Thus, it was found that the cell viability of cells treated with the water-soluble fluorescent fullerene derivative according to the present invention was higher than that of cells treated with inorganic metal-based nanoparticles (S. Cho, D. Maysinger, M. Jain, B. Roder, S. Hackbarth, F. Winnik, *Langumir*, 2007, 23, 1974-1980), such as quantum dots having cell stability at a concentration of about 10 μg/mL or less (see FIG. 11c).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

According to the method of preparing a water-soluble fluorescent fullerene derivative the present invention, a fullerene derivative having strong fluorescence and hydrophilicity is prepared in a simple and easy manner. In addition, the preparation method enables the intensity and wavelength of fluorescence to be easily controlled depending on the amount of fullerene and the kind of catalyst. The prepared fluorescent fullerene derivative contains a biocompatible ligand, and thus is useful as a biological fluorescent dye. In addition, the fluorescent fullerene derivative has not only fluorescence, but also excellent solubility in a solvent, and thus is useful in the biological field, the medical field, the nanotechnology field, etc.

The invention claimed is:

1. A method for preparing a water-soluble fluorescent fullerene derivative, the method comprising the steps of:
    (a) dispersing fullerene in a first solvent to obtain a dispersion;
    (b) mixing the dispersion with a strong base catalyst and a ligand containing a terminal hydroxyl group to obtain a mixture; and
    (c) purifying the mixture, thereby preparing a fluorescent fullerene derivative,
    wherein in step (a), the fullerene is dispersed in the first solvent to a concentration that is in a range of from 0.0001 mg/ml to 10 mg/ml, and the ligand containing a terminal hydroxyl group contains an ethyleneglycol group.

2. The method of claim 1, wherein the first solvent is selected from the group consisting of toluene, benzene, cyclohexane, heptane, iso-ocatane, and mixtures thereof.

3. The method of claim 1, wherein the fullerene is selected from the group consisting of a fullerene having 60-90 carbon atoms and mixtures thereof.

4. The method of claim 1, wherein the ligand containing a terminal hydroxyl group is selected from the group consisting of diethylene glycol, triethylene glycol, tetraethylene glycol, hexaethylene glycol, poly-ethylene glycol having molecular weights of 200, 300, 400 and 600, di(ethylene glycol)benzylether, di(ethylene glycol)ethylether, di(ethylene glycol) hexylether, di(ethylene glycol)butylether, di(ethylene glycol) methylether, diethylene glycol monobutylether, diethylene glycol monoethylether, diethylene glycol monomethylether, and mixtures thereof.

5. The method of claim 1, wherein the catalyst is preferably selected from the group consisting of lithium hydroxide (LiOH), sodium hydroxide (NaOH), potassium hydroxide (KOH), calcium hydroxide ($Ca(OH)_2$), magnesium hydroxide ($Mg(OH)_2$), barium hydroxide, cadmium hydroxide, cesium hydroxide, cobalt hydroxide, copper hydroxide, nickel hydroxide, rubidium hydroxide, ammonium hydroxide, tetramethylammonium hydroxide, tetraethylammonium hydroxide, tetrabutyl ammonium hydroxide, tetrahexylammonium hydroxide, benzyltrimethylammonium hydroxide, hexadecyltrimethylammonium hydroxide, diethyldimethylammonium hydroxide, and mixture thereof.

6. The method of claim 1, wherein in step (b), the ligand containing the terminal hydroxyl group, and the catalyst are used in the amounts of 0.0001-100 parts by weight and 0.0001-100 parts by weight, respectively, based on 100 parts by weight of the dispersion.

7. The method of claim 1, wherein in step (c), a second solvent is added to the mixture, and the fluorescent fullerene derivative is precipitated and is separated from unreacted fullerene and the ligand containing the terminal hydroxyl group.

8. The method of claim 7, wherein the second solvent is selected from the group consisting of non-polar solvents, polar solvents, and mixtures thereof.

* * * * *

UNITED STATES PATENT AND TRADEMARK OFFICE
CERTIFICATE OF CORRECTION

| | | |
|---|---|---|
| PATENT NO. | : 9,079,837 B2 | |
| APPLICATION NO. | : 13/643292 | |
| DATED | : July 14, 2015 | |
| INVENTOR(S) | : Bong Hyun Chung | |

It is certified that error appears in the above-identified patent and that said Letters Patent is hereby corrected as shown below:

In the Claims

Column 10, lines 50-51, Claim 5: "wherein the catalyst is preferably selected" should be
-- wherein the catalyst is selected --.

Signed and Sealed this
Eighth Day of September, 2015

Michelle K. Lee
*Director of the United States Patent and Trademark Office*